United States Patent
El-Zehiry et al.

(10) Patent No.: US 11,169,484 B2
(45) Date of Patent: *Nov. 9, 2021

(54) VIRTUAL STAINING OF CELLS IN DIGITAL HOLOGRAPHIC MICROSCOPY IMAGES USING GENERAL ADVERSARIAL NETWORKS

(71) Applicant: Siemens Healthcare Diagnostics Inc., Tarrytown, NY (US)

(72) Inventors: Noha Youssry El-Zehiry, Plainsboro, NJ (US); Saikiran Rapaka, Pennington, NJ (US); Ali Kamen, Skillman, NJ (US)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 43 days.

This patent is subject to a terminal disclaimer.

(21) Appl. No.: 16/617,597

(22) PCT Filed: Sep. 6, 2018

(86) PCT No.: PCT/US2018/049702
§ 371 (c)(1),
(2) Date: Nov. 27, 2019

(87) PCT Pub. No.: WO2019/060141
PCT Pub. Date: Mar. 28, 2019

(65) Prior Publication Data
US 2020/0183327 A1 Jun. 11, 2020

Related U.S. Application Data

(60) Provisional application No. 62/560,272, filed on Sep. 19, 2017.

(51) Int. Cl.
*G03H 1/00* (2006.01)
*G03H 1/08* (2006.01)
(Continued)

(52) U.S. Cl.
CPC ......... *G03H 1/0005* (2013.01); *G03H 1/0866* (2013.01); *G06K 9/00127* (2013.01);
(Continued)

(58) Field of Classification Search
CPC ............... G03H 1/0005; G03H 1/0866; G03H 2001/005; G06K 9/0012; G06K 9/00147;
(Continued)

(56) References Cited

U.S. PATENT DOCUMENTS 9,501,844 B2  11/2016  Young et al.
10,176,363 B2  1/2019  El-Zehiry et al.
(Continued)

FOREIGN PATENT DOCUMENTS

JP  2014506122 A  3/2014
JP  2017519985 A  7/2017
WO  2015195609  12/2015

OTHER PUBLICATIONS

"Zhu et al. 'Unpaired Image-to-Image Translation using Cycle-Consistent Adversarial Networks', 2017, IEEE International Conference on Computer Vision, pp. 2242-2251" (Year: 2017).*
(Continued)

*Primary Examiner* — Vu Le
*Assistant Examiner* — Julius Chai

(57) ABSTRACT

A cell visualization system includes a digital holographic microscopy (DHM) device, a training device, and a virtual staining device. The DHM device produces DHM images of cells and the virtual staining device colorizes the DHM images based on an algorithm generated by the training device using generative adversarial networks and unpaired training data. A computer-implemented method for producing a virtually stained DHM image includes acquiring an image conversion algorithm which was trained using the generative adversarial networks, receiving a DHM image
(Continued)

with depictions of one or more cells and virtually staining the DHM image by processing the DHM image using the image conversion algorithm. The virtually stained DHM image includes digital colorization of the one or more cells to imitate the appearance of a corresponding actually stained cell.

18 Claims, 7 Drawing Sheets

(51) Int. Cl.
    *G06K 9/00*     (2006.01)
    *G06T 7/00*     (2017.01)

(52) U.S. Cl.
    CPC ..... *G06T 7/0012* (2013.01); *G03H 2001/005* (2013.01); *G06T 2207/30024* (2013.01)

(58) Field of Classification Search
    CPC .............. G06K 2209/05; G06T 7/0012; G06T 2207/30024; G06T 2207/20084; G06T 2207/20081; G06T 2207/10056; G06N 3/08
    See application file for complete search history.

(56) References Cited

U.S. PATENT DOCUMENTS

| | | | |
|---|---|---|---|
| 10,614,287 B2* | 4/2020 | El-Zehiry | G01N 15/1468 |
| 2012/0034647 A1* | 2/2012 | Herzog | G01N 33/49 435/34 |
| 2012/0147002 A1* | 6/2012 | Young | G06T 15/04 345/419 |
| 2014/0056505 A1* | 2/2014 | Hoyt | G06T 7/90 382/133 |
| 2014/0270456 A1* | 9/2014 | Khare | G03H 1/0866 382/133 |
| 2014/0270457 A1 | 9/2014 | Bhargava | |

OTHER PUBLICATIONS

Young et al. (US 20120147002; hereafter: Young) and Zhu et al. ("Unpaired Image-to-Image Translation using Cycle-Consistent Adversarial Network", ARXIV.ORG, Cornell Univsersity Library, 201 Olin Library Cornell University Ithaca, NY 14853, Mar. 30, 2017. (Year: 2017).*

International Search Report dated Dec. 19, 2018 in corresponding International Patent Application No. PCT/US2018/049702.

Marquet, et al.; "Digital holographic 1 microscopy: a noninvasive contrast imaging technique allowing quantitative visualization of 1 livng cells with subwavelength axialaccuracy", Optics Letters, Optical Society of America, US, vol. 30, No. 5. Mar. 2005 (Mar. 2005), pp. 468-470.

Osokin, et al.; "GANs for Biological Image Synthesis",, Sep. 12, 2017 (Sep. 12, 2017), pp. 1-14.

Zhu, et al; "Unpaired Image-to-Image Translation using Cycle-Consistent Adversarial Networks", ARXIV.ORG, Cornell University Library, 201 Olin Library Cornell University Ithaca, NY 14853, Mar. 30, 2017 (Mar. 30, 2017).

Office Action dated Jun. 29, 2021 in corresponding Japanese Patent Application No. 2020-537129.

Osokin, Anton et al: "GANs for Biological Image Synthesis"; Computer Vision and Pattern Recognition, USA, Cornell University; Sep. 12, 2017; pp. 1-14; https://arxiv.org/abs/1708.04692; (Conventional Art Instance).

Han, Liang et al: "Transferring Microscopy Image Modalities with Conditional Generative Adversarial Networks"; 2017 IEEE Conference on Computer Vision and Pattern Recognition Workshops (CVPRW), USA; IEEE; Jul. 21, 2017; pp. 851-859; (Conventional Art Instance).

Ito, K. @itok_msi: "Is it possible to change a dog into a cat by using GAN ? [CYCLEGAN edition (1)]"; Internet, Japan, @itok_msi; Jun. 14, 2017; https://qiita.com/itok_msi/items/b6b615bc28b1a720afd7; (Conventional Art Instance).

* cited by examiner

VIRTUAL STAINING OF CELLS IN DIGITAL HOLOGRAPHIC MICROSCOPY IMAGES USING GENERAL ADVERSARIAL NETWORKS

CROSS-REFERENCE TO RELATED APPLICATIONS

This application is a national phase filing under 35 U.S.C. § 371 of International Patent Application No. PCT/US2018/049702, filed Sep. 6, 2018, which is incorporated herein by reference in its entirety.

TECHNICAL FIELD

The present invention relates generally to virtual staining of cells, and, more particularly, to virtual staining of cells in digital holographic microscopy images using general adversarial networks with cycle consistency.

BACKGROUND

Digital holographic microscopy (DHM), also known as interference phase microscopy, is an imaging technology that provides the ability to quantitatively track sub-nanometric optical thickness changes in transparent specimens. Unlike traditional digital microscopy, in which only intensity (amplitude) information about a specimen is captured, DHM captures both phase and intensity. The phase information, captured as a hologram, can be used to reconstruct extended morphological information (such as depth and surface characteristics) about the specimen using a computer algorithm. Modern DHM implementations offer several additional benefits, such as fast scanning/data acquisition speed, low noise, high resolution and the potential for label-free sample acquisition Off-axis DHM systems create holograms where there is a modulating sinusoidal fringe pattern over the entire field of view due to a small angle between the object and reference beams. In other words, plane waves impinging a sensor surface interfere destructively and constructively at the location of the sensor and thus form the sinusoidal pattern. Furthermore, as depicted in FIG. 1, a reference beam 20 is created from an object beam 10 using a pin hole at the location of the optical Fourier-plane (or conjugated plane to the Fourier-plane) to erase the object spatial signature and to provide a uniform plane waves for creating an interference or hologram image which may be stored and displayed to a user.

DHM is used in hematology to image different cells within a blood sample. When the beam passes through the cell to be imaged, it gets refracted based on the cell characteristics. These refraction variations can be captured through DHM as changes in the optical thickness within the nucleus. In white blood cells (WBCs), namely, basophils, eosinophils, lymphocytes, monocytes and neutrophils, the nuclei and the membranes have different properties and the structure of the cell constituents differ based on the cell type. Thus, the appearance of the DHM image changes depending on the cell type.

DHM images can thus be used to differentiate different types of WBCs within a blood sample. Cell type differentiation and counting of WBCs is an important aspect of a complete blood count (CBC) because, among other reasons, imbalance in certain proportions of the different cell types may indicate different autoimmune diseases and yield different patient diagnoses. Thus, a clinician can use captured DHM images of a blood sample in patient diagnosis.

Conventionally, counts of different WBC types may be obtained by providing a blood sample to an automated machine, such as a laser flow cytometer, which performs an automated count and analysis. In order to confirm or supplement the automated results, or in the absence of an automated machine, blood cells are also manually examined under a microscope and the different types of WBCs are counted and reviewed by a clinician. In order to be able to visually distinguish the different WBC types, the blood sample is stained with a dye before examination, such as through a peripheral blood smear. A blood film may be made by placing a drop of blood on one end of a glass slide and using a spreader to disperse the blood sample into a monolayer over the slide's length. The nucleus of each different type of WBC absorbs the stain differently, for example, as shown in FIG. 2, allowing the clinician to count and examine the different WBCs in a blood smear sample.

The manual blood staining process is time and labor consuming. Each sample must go through the blood smear process and the clinician must look at the sample under the microscope and look for and count the different cell types. This process is inefficient. DHM images have become an alternative to conventional microscopy and can be used to examine a blood sample and count the different types of WBCs in the sample. However, DHM images, such as those shown in the example DHM images of FIG. 3, may not include sufficient detail or resolution in order to allow each cell type to be easily identified and categorized by the clinician.

The present disclosure is directed to overcoming these and other problems of the prior art, such as through providing a cell visualization system that virtually generates stained images from DHM images, replacing or supplementing the need to perform the manual staining process. Moreover, the present disclosure is directed to overcoming a problem of DHM imaging which renders it difficult to train an automated system in determining how to identify and present each virtually-stained cell. In particular, since it is infeasible to obtain the stained image and the corresponding DHM image for the same cell because of the nature of each process, the virtual stain cannot simply be a reproduction of an actual stain. The present disclosure is additionally directed to overcoming this problem associated with training the cell visualization system.

SUMMARY

In one aspect, embodiments of the present disclosure are directed to a computer-implemented method for producing a virtually stained digital holographic microscopy (DHM) image. The method includes acquiring an image conversion algorithm which was trained using generative adversarial networks and receiving a DHM image acquired using a DHM device, the DHM image including depictions of one or more cells. The method further includes virtually staining the DHM image by processing the DHM image using the image conversion algorithm. The virtually stained DHM image includes digital colorization of the one or more cells to imitate the appearance of a corresponding actually stained cell.

In another aspect, embodiments of the present disclosure are directed to another computer-implemented method for producing a virtually stained digital holographic microscopy (DHM) image. The method includes receiving a first training data set comprising DHM images of individual white blood cells and a second training data set comprising images of actually stained white blood cells, wherein the images in the first training data set are not paired with the images in the second training data set. The method also includes applying a learning process which uses generative adversarial networks to the first training data set and the second training data set to generate an image conversion algorithm. The method further includes receiving a DHM image, applying the image conversion algorithm to the DHM image to produce the virtually stained DHM image, and displaying the virtually stained DHM image through a graphical user interface.

In yet another aspect, embodiments of the present disclosure are directed to a cell visualization system configured to produce virtually stained digital holographic microscopy (DHM) images. The cell visualization system includes a virtual staining device configured to receive a DHM image of one or more cells and apply an image conversion algorithm to the DHM image to produce the virtually stained DHM image, where the image conversion algorithm was generated using unpaired data sets.

Additional features and advantages of the invention will be made apparent from the following detailed description of illustrative embodiments that proceeds with reference to the accompanying drawings.

BRIEF DESCRIPTION OF THE DRAWINGS

The foregoing and other aspects of the present invention are best understood from the following detailed description when read in connection with the accompanying drawings. For the purpose of illustrating the invention, there are shown in the drawings embodiments that are presently preferred, it being understood, however, that the invention is not limited to the specific instrumentalities disclosed. Included in the drawings are the following Figures.

DETAILED DESCRIPTION

The present disclosure describes embodiments of apparatuses, systems, and associated methods related to cell visualization using virtual staining of DHM images. In some embodiments, a cell visualization system is configured to receive a blood sample and produce DHM images of cells within the sample, including white blood cells. The cell visualization system may be configured to identify the type of each white blood cell and modify the associated DHM image such that each white blood cell is colorized to imitate what the cell might look like using manual staining and microscopy.

Consistent with disclosed embodiments, the cell visualization system may be trained to classify white blood cells using deep learning algorithms which utilize unpaired data samples. For example, generative adversarial networks with cycle consistency may be used to train the cell visualization system to learn how to identify different types of white blood cells in DHM images and how to colorize the images in order for the white blood cells to appear as if they had been stained in a comparable manual process.

Figure 1:
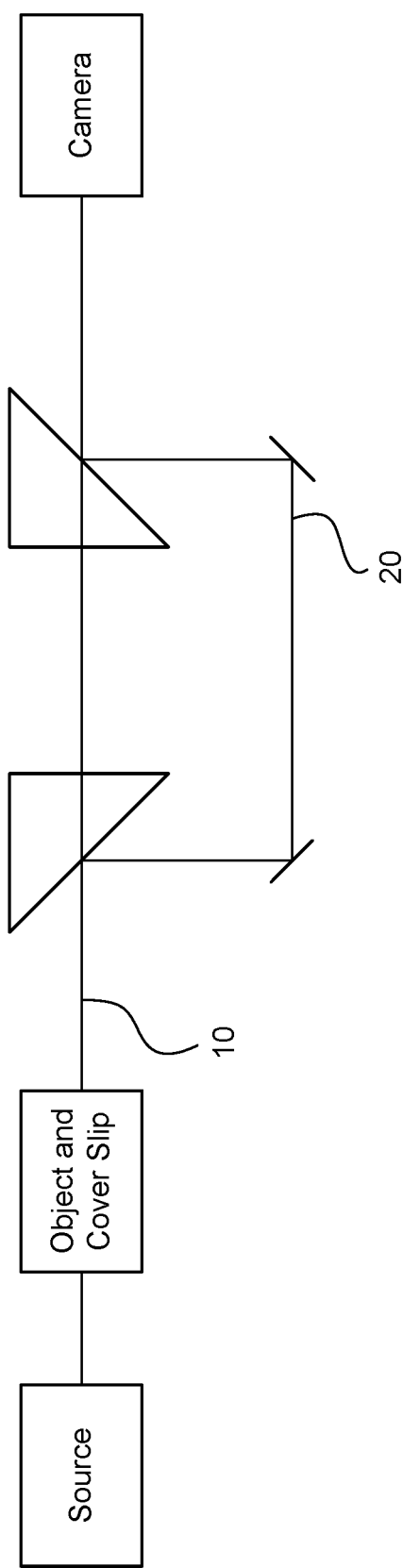
FIG. 1 is an example schematic of off-axis digital holographic microscopy system with a reference beam created from an object beam.
Figure 2:
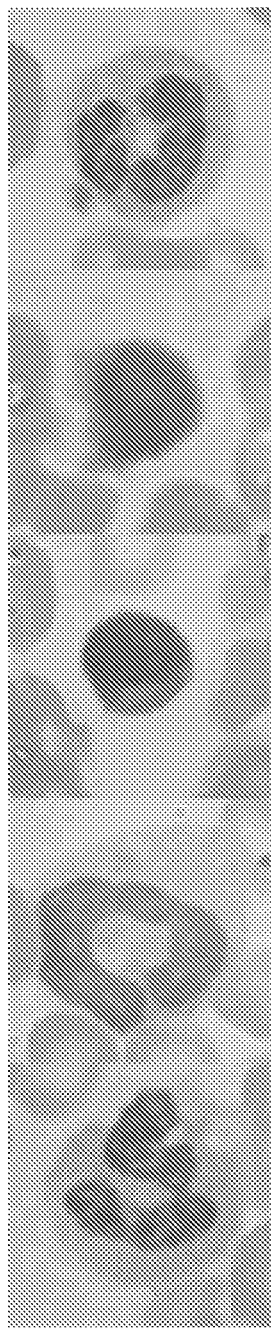
FIG. 2 shows example images of stained white blood cells.
Figure 4A:
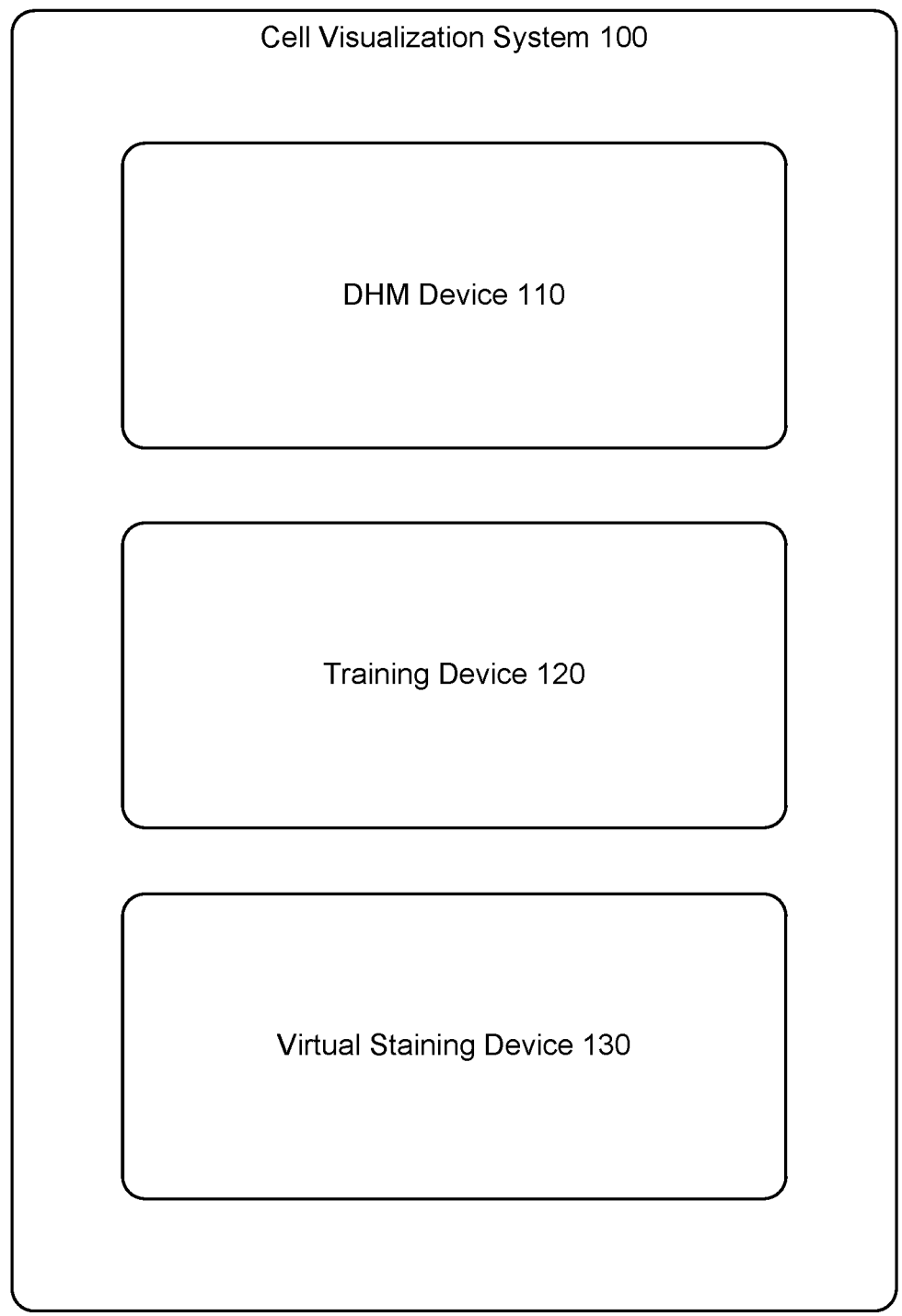
FIGS. 4A-4B show an exemplary cell visualization system, consistent with disclosed embodiments.

FIG. 4A is a diagram of a cell visualization system 100, according to a disclosed embodiment. The cell visualization system 100 includes a DHM device 110, a training device 120, and a virtual staining device 130. The cell visualization system 100 is configured to produce DHM images which are virtually stained to imitate the appearance of cells which have been manually stained and viewed under a conventional microscope (e.g., the images in FIG. 2). FIG. 2 further depicts an exemplary flow of data through the cell visualization system 100 in order to produce the virtually stained DHM images.

Each of the DHM device 110, the training device 120, and virtual staining device 130 may be separate or may be selectively integrated into a combined device. The DHM device 110 includes DHM components known in the art and configured to produce DHM images based on a received blood sample. The training device 120 is configured to receive DHM images and training data, and execute a training process which results in a trained image conversion process. The virtual staining device 130 is configured to receive and execute the trained image conversion process in order to convert DHM images received from the DHM device 110 into virtually stained images. The virtual staining device 130 may be further configured to display the virtually stained images to a user (e.g., a clinician) for review.

Figure 3:
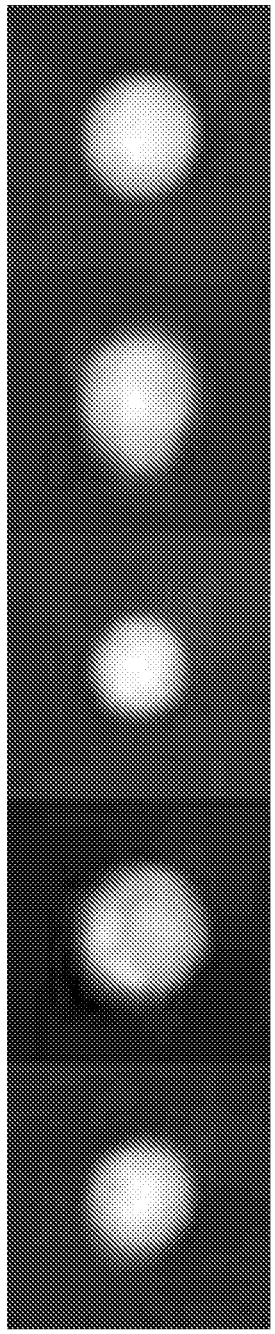
FIG. 3 shows example DHM images of white blood cells.
Figure 4B:
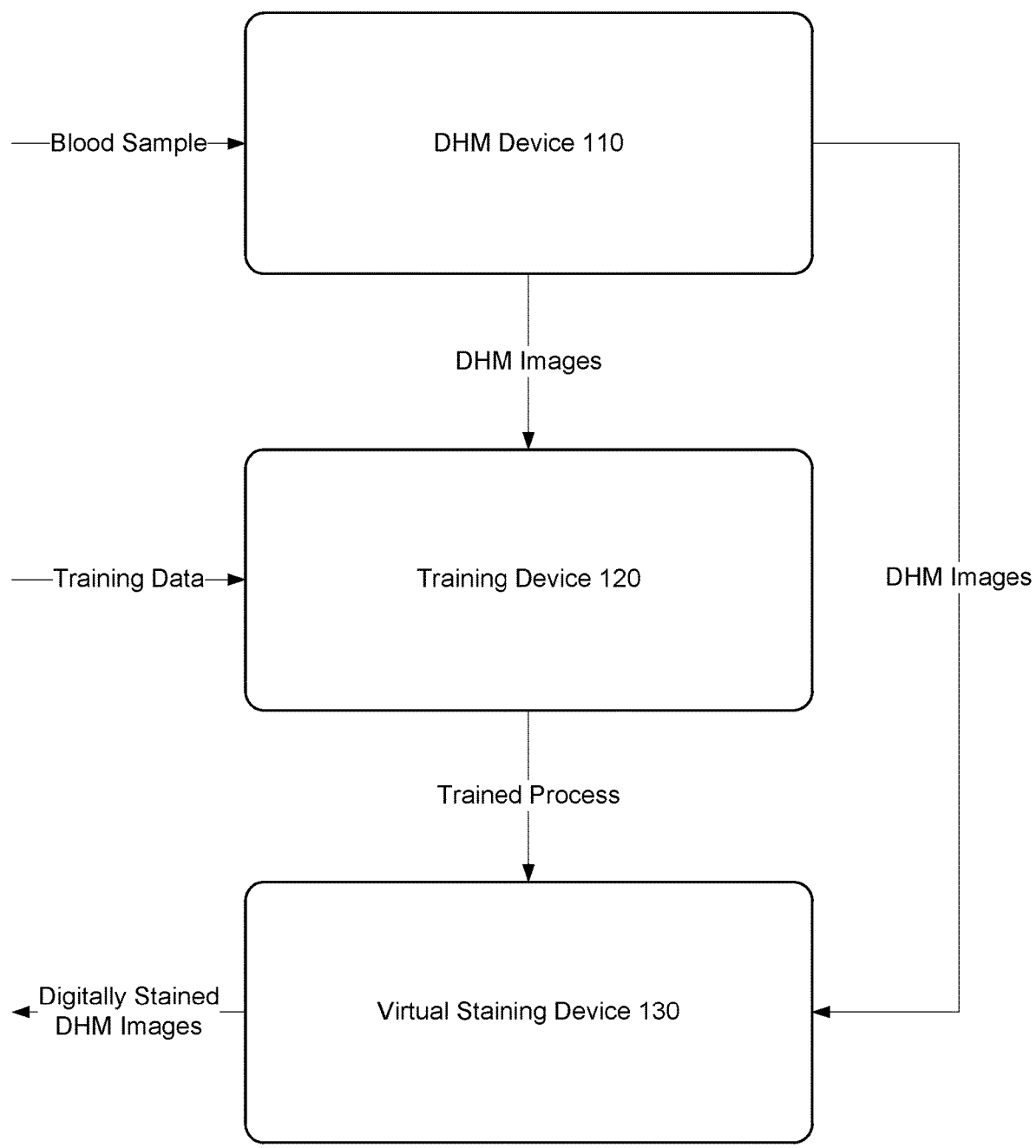

FIG. 4B is a schematic diagram of an exemplary process flow through the cell visualization system 100. The DHM device 110 is configured to produce DHM images of cells, such as those shown in FIG. 3. For example, the DHM device 110 may receive a blood sample and capture periodic data using off-axis DHM while the sample is flowing. The captured data may be converted into DHM images which encompass many cells, including red and white blood cells. These capture images which include many cells may be generally referred to as raw DHM images. In some embodiments, the DHM device 110 is configured to pre-process the raw DHM images in order to separate the raw data into separate images of one or more cells. For example, the DHM device 110 may look for bright spots within the raw DHM images and perform an analysis to identify which of the bright spots are above a size or other classifier threshold in order to identify which of the spots are cells. Each of the classified cells may be transformed into a separate DHM image, resulting in separate cell images such as those shown in FIG. 3.

The training device 120 is configured to receive image data through one or more I/O devices, including an I/O device connected to the DHM device. The training device 120 is also configured to receive training data in the form of other images, which are not DHM images (i.e., images of stained samples) through I/O device(s). The training data may be provided by a different imaging device, such as a device configured to capture images of actually-stained cells, such as those shown in FIG. 2. The training data may also include identifying information associated with the images which is used in the training. For example, each image may include information which identifies the type of cell or cells in the image (e.g., basophils, eosinophils, lymphocytes, monocytes, or neutrophils).

The virtual staining device 130 is configured to communicate with the training device 120 and receives a trained process from the training device 120. In an exemplary embodiment, the trained process is an algorithm, generated by the training device 120 through generative adversarial networks, which converts DHM images into virtually stained DHM images. This conversion is sometimes referred to herein as "virtually staining" the DHM images and, in at least some embodiments, includes digital colorization of the one or more cells to imitate the appearance of a corresponding manually stained cell. The virtual staining device 130 is configured to execute an associated process and produce the virtually stained DHM images for display to a clinician for review. The virtual staining device 130 may be further configured to produce and store data associated with the virtually stained DHM images for analysis and/or use in further processes, such as image filtering, cell counting, cell analysis, etc.

The training device 120 is configured to use generative adversarial networks in order to train the virtual staining device 130 to convert DHM images into virtually stained DHM images. In an exemplary embodiment, the training device 120 uses generative adversarial networks as a training algorithm. Generative adversarial networks generally represent a class of artificial intelligence algorithms that falls under the category of unsupervised learning. In its simplest form, generative adversarial networks are a combination of two neural networks: one network is learning how to generate examples (e.g., virtually stained images) from a training data set (e.g., images of physically stained samples) and another network attempts to distinguish between the generated examples and the training data set. The training process is successful if the generative network produces examples which converge with the actual data such that the discrimination network cannot consistently distinguish between the two.

In generative adversarial networks, training examples consist of two data sets X and Y. The data sets are unpaired, meaning that there is no one-to-one correspondence of the training images in X and Y. The generator network learns how to generate an image y' for any image x in the X data set. More particularly, the generator network learns a mapping G:X→Y which produces an image y' (y'=G(x)). The generator network trains the mapping G:X→Y such that y' is indistinguishable from y by a discriminator network trained to distinguish y' from y. In other words, the generator network continues producing examples until the discriminator network cannot reliably classify the example as being produced by the generator network (y') or supplied as an actual example (y).

There are many different characteristics of images that may result in a successful mapping G:X→Y. As a result, it is possible that the mapping will be successful in fooling the discriminator network without producing images y' which meet the objective. For example, the generative network may produce examples y' which are similar to the images in y, but not in the aspects or characteristics that are important to the viewer.

In order to address this issue, the training device 120 is further configured to use additional constraints which help to ensure cycle consistency during the training process. Cycle consistency refers to a constraint in which the examples y' which are produced by the mapping G:X→Y should be able to be mapped back to x through an inverse mapping F:Y→X. In other words, if an example x is mapped to y' using G, the mapping F should be able to convert y' to an image x' which is identical to the original x. More particularly, the training device 120 learns the inverse mapping F:Y→X such that it produces an image x' (x'=F(y)) which is indistinguishable from x by a discriminator network configured to distinguish x' from x.

In order to train each mapping F, G to produce images which are indistinguishable by the discriminator networks, the training device 120 applies an adversarial loss to each mapping, per the below equations.

$$L_{GAN}(G,D_y,X,Y) = E_{y \sim P_{data(y)}}[\log D_Y(y)] + E_{x \sim P_{data(x)}}[\log(1 - D_y(G(x)))]$$

$$L_{GAN}(F,D_x,X,Y) = E_{x \sim P_{data(x)}}[\log D_x(x)] + E_{y \sim P_{data(y)}}[\log(1 - D_x(F(y)))]$$

In these equations G is a mapping which produces images G(x) which are similar to images in the domain Y. $D_y$ is a discriminator which aims to distinguish between generated examples G(x) and actual examples y in the domain Y. F is an inverse mapping which produces images F(y) which are similar to images in the domain X. $D_x$ is a discriminator which aims to distinguish between generated examples F(y) and actual examples x in the domain X.

In addition to these adversarial losses, the training device 120 is configured to use cycle consistency losses for each mapping G, F. The cycle consistency losses aim to keep the acceptable successful mappings in a realm in which the generated images are cycle consistent in that they can be input into the inverse mapping to reproduce the original image. The cycle consistency losses can be expressed using the below equation.

$$L_{cyc}(F,G) = E_{x \sim P_{data(x)}} \|F(G(x)) - x\| + E_{y \sim P_{data(y)}} \|G(F(y)) - y\|$$

Combining the adversarial losses and the cycle consistency losses together, the full objective can be expressed as the following equation, where λ controls the relative contribution of the cycle consistency losses.

$$L(G,F,D_x,D_y) = L_{GAN}(G,D_y,X,Y) + L_{GAN}(F,D_x,Y,X) + \lambda L_{cyc}(F,G)$$

The full loss can be used to solve the following equation, which results in algorithms G* and F* which translate images from one dataset to another.

$$G^*, F^* = \arg\min_{F,G} \max_{D_x,D_y} L(G, F, D_x, D_y)$$

Consistent with disclosed embodiments, the training device 120 is configured to utilize generative adversarial networks with cycle consistency to produce an algorithm which translates DHM images into virtually stained DHM images. The X data set includes DHM images of white blood cells and the Y data set includes images of stained white blood cells. The mapping F:X→Y represents the translation of images from the X domain into images in the Y domain and the mapping G:Y→X represents the translation of images from the Y domain into images in the X domain.

In cell visualization system 100, the DHM device 110 is configured to produce DHM images and provide the images to the training device 120. In some embodiments, the DHM images may include cropped images of one or more white blood cells. The DHM images form the X domain images of the training data. The images shown in FIG. 3 are examples of these DHM images. The training device 120 also receives images which include stained white blood cells. These stained white blood cell images form the Y domain images of the training data. The images shown in FIG. 2 are examples of these stained cell images. Both sets of images are preferably cropped and sized to a selected image size.

The training device 120 uses these X and Y domain images as input for the generative adversarial networks with cycle consistency process described herein. As a result, the training device produces algorithms F* and G*, where F* translates DHM images into virtually stained DHM images and G* translates stained cell images into virtual DHM images (images of cells which are not stained as they would appear in a DHM images). The F* algorithm is transmitted or otherwise provided to virtual staining device 130. The virtual staining device 130 is configured to execute a virtual staining process using the F* algorithm to convert DHM images into virtually stained DHM images.

The virtually stained DHM images may include images of individual cells or images of multiple cells (such as would be viewed under a microscope during a manual staining process). In order to produce virtually stained images of multiple cells, the DHM device 110 and/or virtual staining device 130 may be configured to segment DHM images of larger cells into individual cells and recombine the segmented images after virtual staining of the individual cells.

Figure 5A:
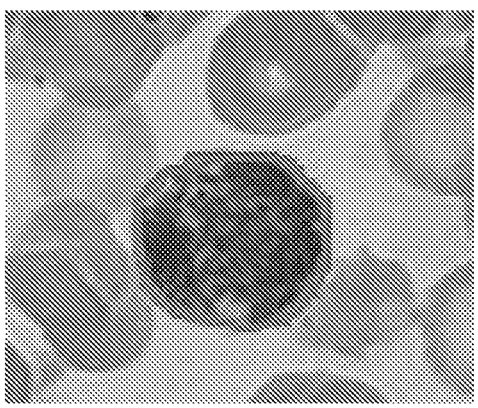
FIGS. 5A-5F show a comparison of images of actually stained white blood cells and virtually stained white blood cells.
Figure 5D:
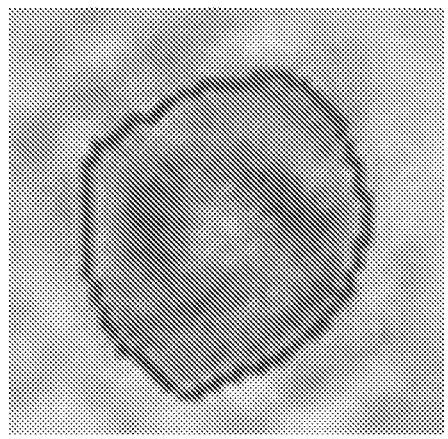
Figure 5B:
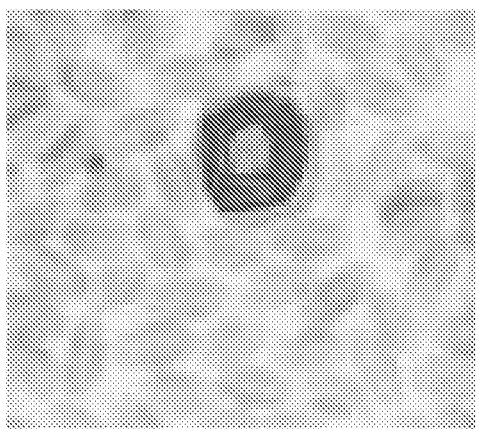
Figure 5E:
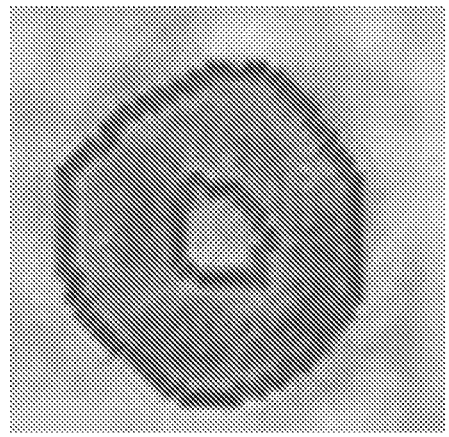
Figure 5C:
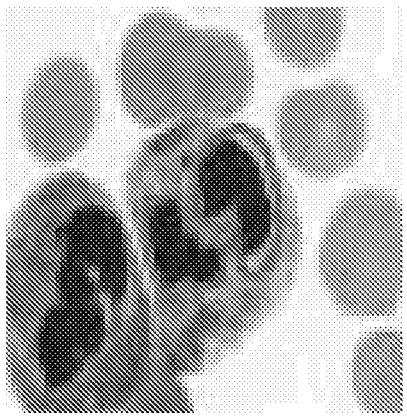
Figure 5F:
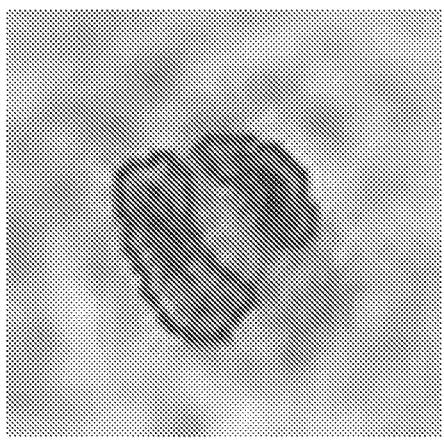

FIGS. 5A, 5B, and 5C illustrate examples of stained cell images and FIGS. 5D, 5E, and 5F illustrate examples of respective corresponding virtually stained DHM images. FIG. 5A illustrates an example of a manually stained Lymphocyte and FIG. 5D illustrates an example of a virtually stained Lymphocyte. FIG. 5B illustrates an example of a manually stained Eosinophil and FIG. 5E illustrates an example of a virtually stained Eosinophil. FIG. 5C illustrates an example of a manually stained Neutrophil and FIG. 5F illustrates an example of a virtually stained Neutrophil. The borderline around each stained portion has been added to the images to emphasize the similarity. It should be understood that the stained cells in FIGS. 5A-5C do not correspond to the same cells in FIGS. 5D-5F. FIGS. 5A-5F illustrate a visual comparison which shows the similarity between virtually stained DHM images and manually stained cells.

In use, the cell visualization system 100 is configured to convert a blood sample into virtually stained DHM images for review by a clinician. In this way, DHM images can be reviewed by the clinician in a similar manner to the way in which manually stained cells are reviewed. However, the virtual staining process is much less time and labor intensive and provides a more efficient method in which stained cells can be obtained for the review by the clinician.

In some embodiments, the cell visualization system 100 (e.g., the virtual staining device 130) may include a cell classification unit which is configured to review the virtually stained DHM images and classify the cell type (e.g., basophil, eosinophil, lymphocyte, monocyte or neutrophil). The cell classification unit may be trained to determine the cell type based on the presentation of the virtual stain in the virtually stained DHM image. The cell type may be stored as data with the virtually stained DHM images. The cell visualization system 100 can use the identification data to produce useful information, such as cell type count and proportions. Moreover, the cell visualization system 100 can use the identification data to identify abnormalities which can be prioritized and presented to clinician for review. Moreover, the cell visualization system 100 may use the identification data to filter the virtually stained DHM images, allowing a clinician to selectively review certain images.

The virtually stained image data produced by the cell visualization system 100 can be used in several advantageous ways. For example, because virtual staining does not require a microscope to view or capture the images, the virtually stained DHM images can be conveniently provided to a clinician in any format and at any location. For example, the virtually stained DHM images can be generated at one location and provided to a clinician anywhere in the world. The clinician does not need to use a microscope to view the images, and instead can review the images on any platform, including a personal computer or mobile device. For example, the outcome of a virtual staining process can be uploaded to a cloud based system and the images can be immediately viewed by the clinicians on mobile apps anywhere and anytime without having to be in the lab.

Virtual staining can also be beneficial because of the ease in which data can be produced for other uses. Due to the time and labor intensiveness of manual staining and the capturing of images of these cells, it is difficult to obtain large data sets of stained cell images. Virtual staining of DHM images addresses this problem because stained cell images can be produced at a much greater scale in a shorter amount of time. The availability of larger data sets can help other processes.

For example, virtually stained DHM images can be used to improve classification of the different types of white blood cells. Deep learning algorithms have been used to classify stained white blood cell images. Deep learning methods are known to provide better classification results when more data is used. Virtual staining can be used to generate stained cell images that can be used to augment the training data sets and provide a larger data set to train classification algorithms.

Similarly, the speed with which stained cell images can be produced is beneficial in many areas. For example, virtual staining can create a more efficient pipeline for detecting diseases such as Malaria. In this example, if the doctor suspects Malaria and one test comes out negative, the patient is required to have repeated blood smear tests (thick and thin smears) every 8 hours for two days. This process is time and labor consuming due to the manual staining process. Instead, virtual staining of DHM images can be used for a more efficient pipeline of identifying Malaria parasites.

Moreover, it should be understood that the present disclosure is not limited to the disclosed embodiments. For example, other embodiments may be implemented to produce virtually stained DHM images other than white blood cells. For example, a visualization system can include a similar training device which can be trained based on other image data sets which are related based on a manual stain. For example, a data set can include stained bacterial cells to which distinguish different types of bacteria such that a visualization system can produce virtually stained bacteria images for review by a clinician.

Figure 6:
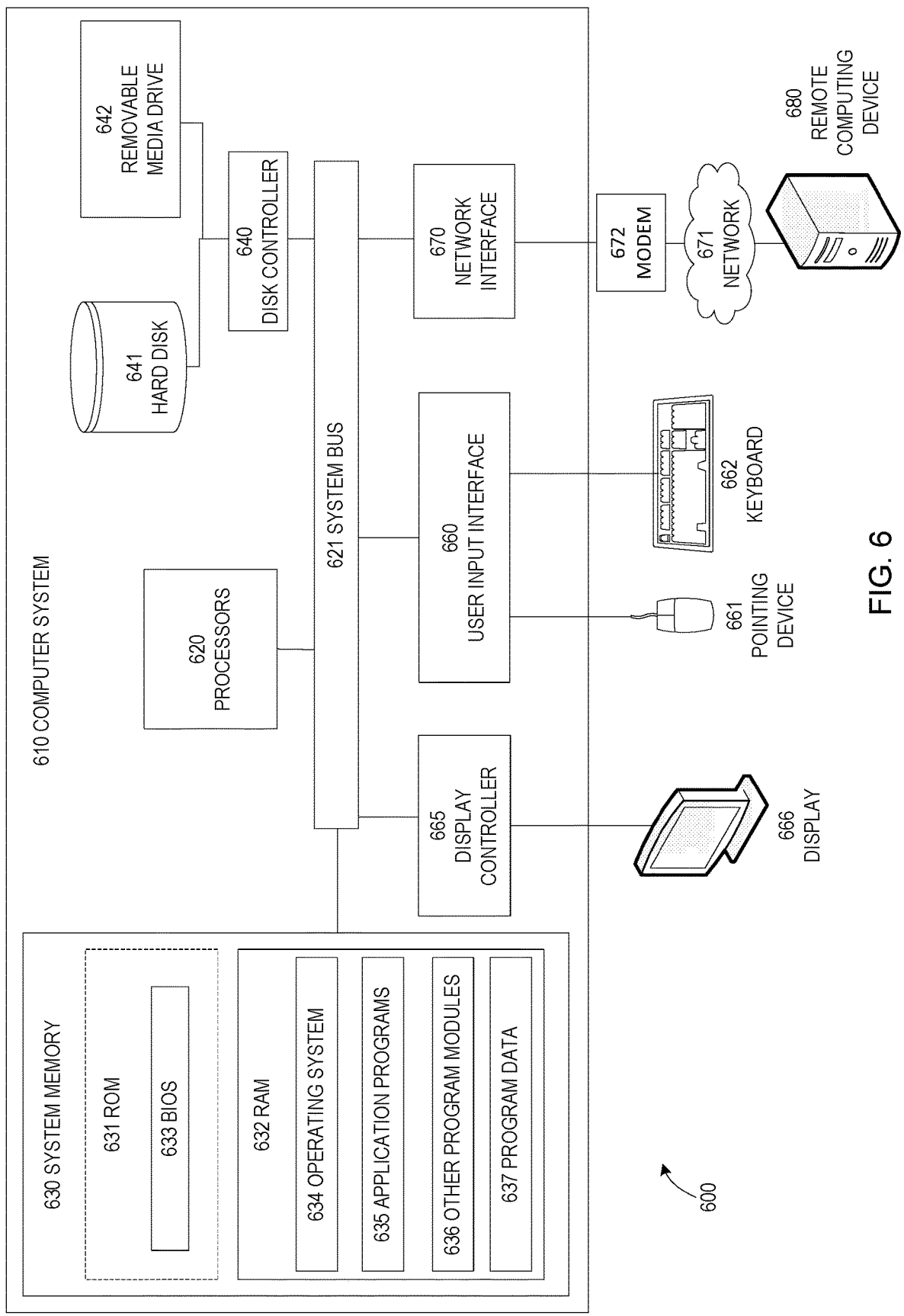
FIG. 6 illustrates an exemplary computing environment within which embodiments of the invention may be implemented.

FIG. 6 illustrates an exemplary computing environment 600 within which embodiments of the invention may be implemented. For example, this computing environment 600 may be configured to execute one or more of the components of an image capture process by the DHM device 110, a training process implemented by the training device 120, or an image conversion process implemented by the virtual staining device 130. The computing environment 600 may include computer system 610, which is one example of a computing system upon which embodiments of the invention may be implemented. Computers and computing environments, such as computer system 610 and computing environment 600, are known to those of skill in the art and thus are described briefly here.

As shown in FIG. 6, the computer system 610 may include a communication mechanism such as a bus 621 or other communication mechanism for communicating information within the computer system 610. The computer system 610 further includes one or more processors 620 coupled with the bus 621 for processing the information. The processors 620 may include one or more central processing units (CPUs), graphical processing units (GPUs), or any other processor known in the art.

The computer system 610 also includes a system memory 630 coupled to the bus 621 for storing information and instructions to be executed by processors 620. The system memory 630 may include computer readable storage media in the form of volatile and/or nonvolatile memory, such as read only memory (ROM) 631 and/or random access memory (RAM) 632. The system memory RAM 632 may include other dynamic storage device(s) (e.g., dynamic RAM, static RAM, and synchronous DRAM). The system memory ROM 631 may include other static storage device (s) (e.g., programmable ROM, erasable PROM, and electrically erasable PROM). In addition, the system memory 630 may be used for storing temporary variables or other intermediate information during the execution of instructions by the processors 620. A basic input/output system (BIOS) 633 containing the basic routines that help to transfer information between elements within computer system 610, such as during start-up, may be stored in ROM 631. RAM 632 may contain data and/or program modules that are immediately accessible to and/or presently being operated on by the processors 620. System memory 630 may additionally include, for example, operating system 634, application programs 635, other program modules 636 and program data 637.

The computer system 610 also includes a disk controller 640 coupled to the bus 621 to control one or more storage devices for storing information and instructions, such as a hard disk 641 and a removable media drive 642 (e.g., floppy disk drive, compact disc drive, tape drive, and/or solid state drive). The storage devices may be added to the computer system 610 using an appropriate device interface (e.g., a small computer system interface (SCSI), integrated device electronics (IDE), Universal Serial Bus (USB), or FireWire).

The computer system 610 may also include a display controller 665 coupled to the bus 621 to control a display 666, such as a cathode ray tube (CRT) or liquid crystal display (LCD), for displaying information to a computer user. The computer system includes an input interface 660 and one or more input devices, such as a keyboard 662 and a pointing device 661, for interacting with a computer user and providing information to the processor 620. The pointing device 661, for example, may be a mouse, a trackball, or a pointing stick for communicating direction information and command selections to the processor 620 and for controlling cursor movement on the display 666. The display 666 may provide a touch screen interface which allows input to supplement or replace the communication of direction information and command selections by the pointing device 661.

The computer system 610 may perform a portion or all of the processing steps of embodiments of the invention in response to the processors 620 executing one or more sequences of one or more instructions contained in a memory, such as the system memory 630. Such instructions may be read into the system memory 630 from another computer readable medium, such as a hard disk 641 or a removable media drive 642. The hard disk 641 may contain one or more datastores and data files used by embodiments of the present invention. Datastore contents and data files may be encrypted to improve security. The processors 620 may also be employed in a multi-processing arrangement to execute the one or more sequences of instructions contained in system memory 630. In alternative embodiments, hard-wired circuitry may be used in place of or in combination with software instructions. Thus, embodiments are not limited to any specific combination of hardware circuitry and software.

As stated above, the computer system 610 may include at least one computer readable medium or memory for holding instructions programmed according to embodiments of the invention and for containing data structures, tables, records, or other data described herein. The term "computer readable medium" as used herein refers to any medium that participates in providing instructions to the processor 620 for execution. A computer readable medium may take many forms including, but not limited to, non-volatile media, volatile media, and transmission media. Non-limiting examples of non-volatile media include optical disks, solid state drives, magnetic disks, and magneto-optical disks, such as hard disk 641 or removable media drive 642. Non-limiting examples of volatile media include dynamic memory, such as system memory 630. Non-limiting examples of transmission media include coaxial cables, copper wire, and fiber optics, including the wires that make up the bus 621. Transmission media may also take the form of acoustic or light waves, such as those generated during radio wave and infrared data communications.

The computing environment 600 may further include the computer system 610 operating in a networked environment using logical connections to one or more remote computers, such as remote computer 680. Remote computer 680 may be a personal computer (laptop or desktop), a mobile device, a server, a router, a network PC, a peer device or other common network node, and typically includes many or all of the elements described above relative to computer system 610. When used in a networking environment, computer system 610 may include modem 672 for establishing communications over a network 671, such as the Internet. Modem 672 may be connected to bus 621 via user network interface 670, or via another appropriate mechanism.

Network 671 may be any network or system generally known in the art, including the Internet, an intranet, a local area network (LAN), a wide area network (WAN), a metropolitan area network (MAN), a direct connection or series of connections, a cellular telephone network, or any other network or medium capable of facilitating communication between computer system 610 and other computers (e.g., remote computer 680). The network 671 may be wired, wireless or a combination thereof. Wired connections may be implemented using Ethernet, Universal Serial Bus (USB), RJ-11 or any other wired connection generally known in the art. Wireless connections may be implemented using Wi-Fi, WiMAX, and Bluetooth, infrared, cellular networks, satellite or any other wireless connection methodology generally known in the art. Additionally, several networks may work alone or in communication with each other to facilitate communication in the network 671.

As one application of the exemplary computing environment 600 to the technology described herein, consider an example system for analyzing DHM data which includes a network component, an image processing processor, and a GUI. The networking component may include network interface 670 or some combination of hardware and software offering similar functionality. The networking component is configured to communicate with a DHM system to retrieve DHM images. Thus, in some embodiments, the networking component may include a specialized interface for communicating with DHM systems. The image processing processor is included in a computing system (e.g., computer system 610) and is configured with instructions that enable to extract a reference image either from single object image or a time series of images received via the networking component, extract the regions from the object image where the fringe patterns are disturbed, and replace those regions with patterns existing from other parts of the image. The image processing processor may include additional functionality, as described in this disclosure, to support this task (e.g., segmentation, filling areas, etc.). The GUI may then be presented on a display (e.g., display 666) for review by a user.

The embodiments of the present disclosure may be implemented with any combination of hardware and software. In addition, the embodiments of the present disclosure may be included in an article of manufacture (e.g., one or more computer program products) having, for example, computer-readable, non-transitory media. The media has embodied therein, for instance, computer readable program code for providing and facilitating the mechanisms of the embodiments of the present disclosure. The article of manufacture can be included as part of a computer system or sold separately.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

An executable application, as used herein, comprises code or machine readable instructions for conditioning the processor to implement predetermined functions, such as those of an operating system, a context data acquisition system or other information processing system, for example, in response to user command or input. An executable procedure is a segment of code or machine readable instruction, sub-routine, or other distinct section of code or portion of an executable application for performing one or more particular processes. These processes may include receiving input data and/or parameters, performing operations on received input data and/or performing functions in response to received input parameters, and providing resulting output data and/or parameters.

A graphical user interface (GUI), as used herein, comprises one or more display images, generated by a display processor and enabling user interaction with a processor or other device and associated data acquisition and processing functions. The GUI also includes an executable procedure or executable application, such as a mobile application on a mobile device. The executable procedure or executable application conditions the display processor to generate signals representing the GUI display images. These signals are supplied to a display device which displays the image for viewing by the user. The processor, under control of an executable procedure or executable application, manipulates the GUI display images in response to signals received from the input devices. In this way, the user may interact with the display image using the input devices, enabling user interaction with the processor or other device.

The functions and process steps herein may be performed automatically or wholly or partially in response to user command. An activity (including a step) performed automatically is performed in response to one or more executable instructions or device operation without user direct initiation of the activity.

The system and processes of the figures are not exclusive. Other systems, processes and menus may be derived in accordance with the principles of the invention to accomplish the same objectives. Although this invention has been described with reference to particular embodiments, it is to be understood that the embodiments and variations shown and described herein are for illustration purposes only. Modifications to the current design may be implemented by those skilled in the art, without departing from the scope of the invention. As described herein, the various systems, subsystems, agents, managers and processes can be implemented using hardware components, software components, and/or combinations thereof. No claim element herein is to be construed under the provisions of 35 U.S.C. 112(f) unless the element is expressly recited using the phrase "means for."

The invention claimed is:

1. A computer-implemented method for producing a virtually stained digital holographic microscopy (DHM) image, comprising:
   receiving a DHM image acquired using a DHM device, the DHM image comprising depictions of a plurality of cells; and
   segmenting the DHM image into a plurality of segmented images, each segmented image depicting an individual cell;
   virtually staining the plurality of segmented images by processing each segmented image using an image conversion algorithm, wherein the image conversion algorithm is generated using unpaired data sets,
   recombining the virtually stained plurality of segmented images to generate a virtually stained DHM image;
   wherein the virtually stained DHM image includes digital colorization of the plurality of cells to imitate the appearance of a corresponding actually stained cell.

2. The computer-implemented method of claim 1, wherein the image conversion algorithm is trained using generative adversarial networks.

3. The computer-implemented method of claim 2, wherein the image conversion algorithm is trained using an adversarial loss and a cycle consistency loss.

4. The computer-implemented method of claim 1, wherein virtually staining the DHM images includes colorization of white blood cells based on the type of each white blood cell.

5. The computer-implemented method of claim 4, further comprising quantifying a ratio of types of white blood cells within a sample based on the colorization of the white blood cells.

6. The computer-implemented method of claim 1, wherein the plurality of cells include bacteria cells and colorization of the bacteria cells depends on the type of bacteria.

7. The computer-implemented method of claim 1, further comprising displaying the virtually stained DHM image through a graphical user interface.

8. A computer-implemented method for producing a virtually stained digital holographic microscopy (DHM) image, comprising:
   receiving a first training data set comprising DHM images of individual white blood cells and a second training data set comprising images of actually stained white blood cells, wherein the images in the first training data set are not paired with the images in the second training data set;
   applying a learning process to the first training data set and the second training data set to generate an image conversion algorithm using generative adversarial networks;

applying the image conversion algorithm to a DHM image to produce the virtually stained DHM image; and displaying the virtually stained DHM image through a graphical user interface.

9. The computer-implemented method of claim 8, wherein the generative adversarial networks comprise a first generative network configured to generate a plurality of virtually stained DHM images and a first discriminating network configured to distinguish between the plurality of virtually stained DHM images and images in the second training data set.

10. The computer-implemented method of claim 9, wherein the generative adversarial networks further comprise a second generative network configured to generate a plurality of virtual DHM images and a second discriminating network configured to distinguish between the plurality of virtual DHM images and images in the first training data set.

11. The computer-implemented method of claim 8, wherein the learning process uses an adversarial loss and a cycle consistency loss to generate the image conversion algorithm.

12. The computer-implemented method of claim 8, wherein the graphical user interface is a mobile application executed on a mobile device.

13. A cell visualization system configured to produce virtually stained digital holographic microscopy (DHM) images, comprising:
 a device configured to receive a DHM image of one or more cells and apply an image conversion algorithm to the DHM image to produce a virtually stained DHM image; and
 a training device configured to generate the image conversion algorithm using the unpaired data sets, the unpaired data sets including a first training data set comprising DHM images of individual cells and a second training data set comprising images of actually stained cells,
 wherein the image conversion algorithm is generated using unpaired data sets, wherein the virtually stained DHM image includes digital colorization of the one or more cells to imitate an appearance of a corresponding actually stained cell.

14. The cell visualization system of claim 13, wherein the training device is configured with generative adversarial networks to generate the image conversion algorithm.

15. The cell visualization system of claim 14, wherein the generative adversarial networks comprise:
 a first generative network configured to generate examples of virtually stained DHM images and a first discriminating network configured to distinguish between the examples of virtually stained DHM images and images in the second training data set; and
 a second generative network configured to generate examples of virtual DHM images and a second discriminating network configured to distinguish between the examples of virtual DHM images and images in the first training data set.

16. The cell visualization system of claim 13, further comprising a DHM device configured to provide the first training data set to the training device.

17. The cell visualization system of claim 16, wherein the DHM device is further configured to provide the DHM image of one or more cells to a virtual staining device.

18. The cell visualization system of claim 13, wherein the one or more cells are white blood cells.

* * * * *